United States Patent
Grass et al.

(10) Patent No.: US 6,785,356 B2
(45) Date of Patent: Aug. 31, 2004

(54) FLUOROSCOPIC COMPUTED TOMOGRAPHY METHOD

(75) Inventors: Michael Grass, Hamburg (DE); Thomas Koehler, Norderstedt (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 141 days.

(21) Appl. No.: 10/293,671

(22) Filed: Nov. 13, 2002

(65) Prior Publication Data

US 2003/0091143 A1 May 15, 2003

(30) Foreign Application Priority Data

Nov. 13, 2001 (DE) .......................................... 101 55 590

(51) Int. Cl.[7] .............................................. A61B 6/00
(52) U.S. Cl. .......................................... 378/4; 378/901
(58) Field of Search ........................... 378/4, 8, 15, 19, 378/901

(56) References Cited

FOREIGN PATENT DOCUMENTS

EP         0 948 930 A1   10/1999
EP         0 990 892 A2 A3   4/2000

OTHER PUBLICATIONS

A fast and efficient method for sequential cone–beam tomography, Kohler, Th.; Proksa, R.; Grass, M.; Nuclear Science Symposium Conference Record, 2000 IEEE, vol. 2, Oct. 15–20 2000 pp. 15/110 –15/112 vol. 2.*

* cited by examiner

Primary Examiner—David V. Bruce
Assistant Examiner—Courtney Thomas
(74) Attorney, Agent, or Firm—Thomas M. Lundin (57) ABSTRACT

The invention relates to a fluoroscopic computed tomography method in which measuring values are continuously acquired so as to be subjected to rebinning and filtering, after which CT images are reconstructed therefrom in a dense temporal sequence. The backprojection comprises the filtered data of fan beams which, while taking into account the data from diametrically oppositely situated zones, cover an overall projection angle range of 180°.

3 Claims, 4 Drawing Sheets

FLUOROSCOPIC COMPUTED TOMOGRAPHY METHOD

BACKGROUND

The invention relates to a fluoroscopic computed tomography method, to a computed tomography apparatus for carrying out such a method, and to a computer program for the processing of the measuring values produced by such a tomography apparatus.

EP 948930 describes a fluoroscopy system which can at the same time be used as a CT system (CT=computed tomography) for forming a three-dimensional CT image (volume CT). The fluoroscopy system comprises a gantry with a radiation source and a flat detector which rotate once about an axis of rotation within a time interval of between 5 and 90 seconds, thus producing from 300 to 500 two-dimensional fluoroscopic images wherefrom a three-dimensional CT image can be reconstructed.

However, in the context of the present invention fluoroscopic computed tomography is to be understood as a method which forms not only a single three-dimensional CT image, but also continuous CT images which are three-dimensional representations at successive imaging instants of the object to be examined, the distance in time between two successive instants being smaller than the period of time required for a rotation of the object to be examined (in the case of industrial objects) or the radiation source (in the case of medical examinations) about the axis of rotation.

A method of this kind is required, for example, for a CT-guided biopsy where a biopsy needle is introduced into an object to be examined and the progress of this biopsy needle is continuously checked on the basis of a series of three-dimensional CT images. For such examinations it is important that the CT images represent an as wide as possible zone of the object to be examined and that they contain as few motional artefacts as possible. The motional artefacts are caused by the fact that the reconstruction utilizes measuring values acquired at different instants.

SUMMARY

Therefore, it is an object of the invention to provide a computed tomography method which meets the described requirements. This object is achieved in accordance with the invention by means of a fluoroscopic computed tomography method which includes the steps of:

continuously irradiating an object to be examined by means of a conical radiation beam which is emitted by a radiation source while the object to be examined or the radiation source rotates about an axis of rotation, continuously acquiring, while using a detector unit, measuring values which are dependent on the intensity in the radiation beam beyond the object to be examined, continuously reconstructing CT images which represent the object to be examined at imaging instants which are situated at a distance in time from one another which is shorter than the period of time required for a rotation of the object to be examined or the radiation source about the axis of rotation, the reconstruction including the following steps:

a) rebinning the measuring values so as to form a number of groups, each group containing the measuring values of fan beams which are formed during the irradiation and are situated in planes extending parallel to one another and to the axis of rotation, b) one-dimensional filtering of the data of each group as produced by the rebinning in order to produce filtered data, c) backprojecting the filtered data of a plurality of groups, for each voxel to be reconstructed there being used filtered data from the last fan beams formed prior to the relevant imaging instant, said fan beams having irradiated the relevant voxel from an overall projection angle range of 180°.

A computed tomography method which includes the steps a) and b) is known from an article by Grass et al in Phys. Med. Biol. 45(2) 329–347 or from the EP-A 990892. In the cited publications it is explained that there is a central, cylindrical zone which has flat side faces extending perpendicularly to the axis of rotation and within which each voxel is irradiated by the radiation source from an angular range of at least 180°. Reconstruction of the attenuation of the radiation cannot be performed with adequate quality outside this zone. The central zone, therefore, is the largest possible zone with flat side faces for which a CT image can be reconstructed. This aspect is used for the invention.

The cited publications elucidate that the central zone contains a first sub-volume which extends perpendicularly to the axis of rotation and is conically tapered towards the sides, the voxels present therein being exposed to radiation in all positions of the radiation source, and also contains a second sub-volume whose voxels are not exposed to the radiation in all radiation source positions. According to the known method, filtered data of fan beams which have irradiated the relevant voxel from an overall projection angle range of 360° are used for each voxel to be reconstructed in the first sub-volume. However, in accordance with the invention for each voxel only filtered data of fan beams which have most recently irradiated the relevant voxel from an overall projection angle range of 180° are used for the two sub-zones of the central zone. The period of time required for the acquisition of the fan beams used for the reconstruction is then shorter than in the known method, so that the artefacts caused by motion during the acquisition of the fan beams are less pronounced.

As has already been stated, the zone which can be reconstructed contains a sub-volume whose voxels are not continuously exposed to a fan beam. A part of the voxels in this sub-volume is exposed to all fan beams in an angular range of 180° as the last fan beams prior to the imaging instant. The reconstruction for these voxels is analogous to the reconstruction for the voxels continuously exposed to fan beams. The other voxels of this second sub-volume are exposed to all fan beams which have been acquired in an angular range of 180° as the last fan beams prior to the imaging instant. Therefore, in order to reconstruct these voxels it is necessary to use fan beams which are situated further back so that an overall projection angle range of 180° is obtained for the fan beams used for the reconstruction of these voxels.

In these cases there may be groups of fan beams which are situated diametrically opposite one another. The invention describes alternative solutions for the processing of the filtered data of these fan beams. The solution in conformity with one aspect of the invention offers a potentially better signal-to-noise ratio because the filtered data of both fan beams is used, whereas the solution in conformity with another aspect potentially involves less motional artefacts because the filtered data of the fan beam acquired earlier is not taken into account.

In accordance with another aspect of the present invention a computed tomography apparatus is provided for carrying out the method of the present invention. In accordance with another aspect of the present invention, a computer program is provided for the processing of the measuring values of a computed tomography apparatus as set forth in accordance with the present invention.

In accordance with one aspect of the invention, a fluoroscopic computed tomography method is provided. The method includes the steps of continuously irradiating an object to be examined by means of a conical radiation beam which is emitted by a radiation source while the object to be examined or the radiation source rotates about an axis of rotation, continuously acquiring, while using a detector unit, measuring values which are dependent on the intensity in the radiation beam beyond the object to be examined, continuously reconstructing CT images which represent the object to be examined at imaging instants which are situated at a distance in time from one another which is shorter than the period of time required for a rotation of the object to be examined or the radiation source about the axis of rotation. The reconstruction includes the following steps: rebinning the measuring values so as to form a number of groups, each group containing the measuring values of fan beams which are formed during the irradiation and are situated in planes extending parallel to one another and to the axis of rotation; one-dimensional filtering of the data of each group as produced by the rebinning in order to produce filtered data; backprojecting the filtered data of a plurality of groups, for each voxel to be reconstructed there being used filtered data from the last fan beams formed prior to the relevant imaging instant, said fan beams having irradiated the relevant voxel from an overall projection angle range of 180°.

In accordance with a more limited aspect of the invention, the filtered data of fan beams which have irradiated the relevant voxel from projection angle ranges ($\phi_A$–$\phi_B$ and $\phi_D$–$\phi_E$) which have been shifted 180° relative to one another and are situated within the overall projection angle range of 180° are summed in a weighted fashion in order to reconstruct the absorption of voxels which are only temporarily present in the fan beam.

In accordance with a more limited aspect of the invention, the reconstruction of the absorption in voxels which are only temporarily present in the fan beam utilizes, from among the filtered data of the fan beams which have irradiated the voxel from directions which are shifted 180° relative to one another and are situated within the overall projection angle range of 180°, only the data ($\phi_A$–$\phi_B$) of the last fan beam formed.

In accordance with another aspect of the invention, a computed tomography apparatus for carrying out the method of the invention is provided. The apparatus includes: a radiation source (S) for continuously generating a conical radiation beam; a drive device for realizing a circular relative motion between the radiation source and the object to be examined; a detector unit for the continuous acquisition of measuring values which are dependent on the attenuation of the rays in the examination zone; and a reconstruction unit for the continuous reconstruction of CT images which represent the object to be examined at imaging instants whose distance in time from one another is shorter than the period of time required for a rotation of the object to be examined or the radiation source about the axis of rotation. The reconstruction unit processes the measuring values as follows: rebinning the measuring values so as to form a number of groups, each group containing the measuring values of fan beams which are formed during the irradiation and are situated in planes extending parallel to one another and to the axis of rotation; one-dimensional filtering of the data of each group as produced by the rebinning in order to produce filtered data; backprojecting the filtered data of a plurality of groups, for each voxel to be reconstructed there being used filtered data from the last fan beams formed prior to the relevant imaging instant, said fan beams having irradiated the relevant voxel from an overall projection angle range of 180°.

In accordance with another aspect of the invention, a computer program for processing the measuring values of a computed tomography apparatus of the present invention is provided. The program includes the steps of: rebinning the measuring values so as to form a number of groups, each group containing the measuring values of fan beams which are formed during the irradiation and are situated in planes extending parallel to one another and to the axis of rotation; one-dimensional filtering of the data of each group as produced by the rebinning in order to produce filtered data; backprojecting the filtered data of a plurality of groups, for each voxel to be reconstructed there being used filtered data from the last fan beams formed prior to the relevant imaging instant, said fan beams having irradiated the relevant voxel from an overall projection angle range of 180°.

DRAWINGS

The invention will be described in detail hereinafter with reference to the drawing. Therein.

DESCRIPTION

Figure 1:
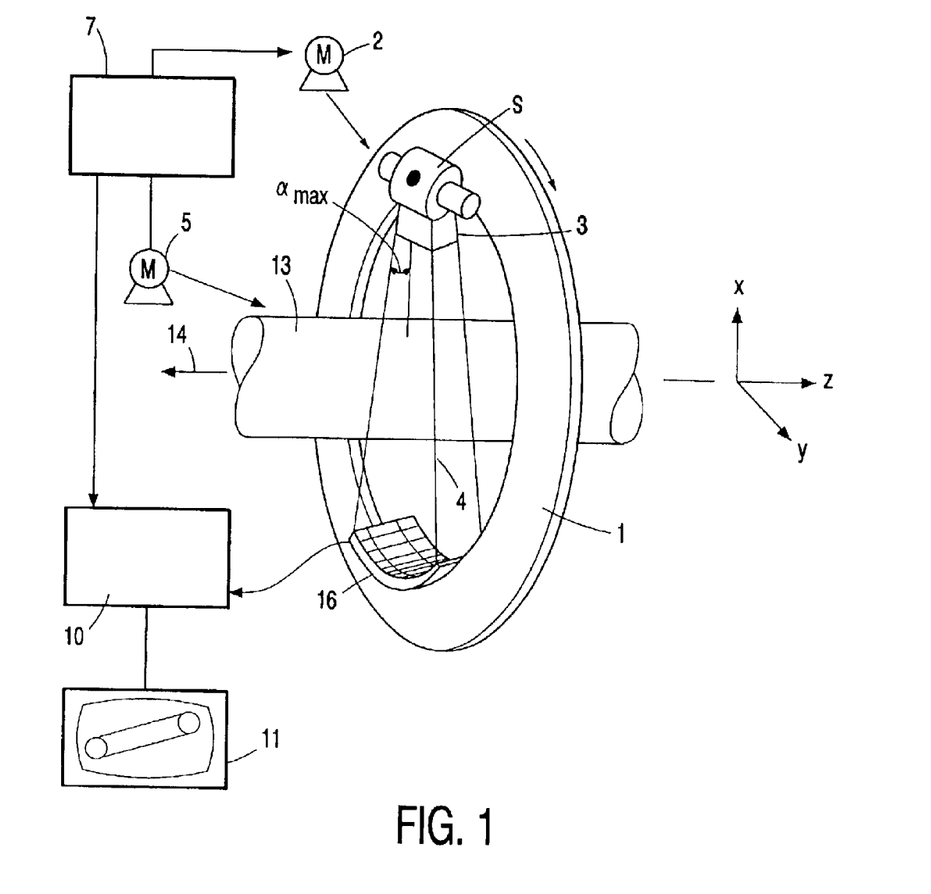
FIG. 1 shows a computed tomography apparatus for carrying out the method in accordance with the invention.

The computed tomography apparatus shown in FIG. 1 includes a gantry 1 which is capable of rotation about an axis of rotation 14 which extends parallel to the z direction of the co-ordinate system shown in FIG. 1. To this end, a motor 2 drives the gantry at a preferably constant but adjustable angular speed. A radiation source S, for example, an X-ray source, is connected to the gantry. The source is provided with a collimator device 3 which forms a conical radiation beam 4 from the radiation produced by the radiation source S, that is, a radiation beam which has a finite dimension other than zero in the z direction as well as in a direction perpendicular thereto (that is, in a plane perpendicular to the axis of rotation).

The radiation beam 4 traverses an examination zone 13 in which an object to be examined, for example, a patient accommodated on a patient table (both not being shown), may be situated. The examination zone 13 is shaped as a cylinder. After having traversed the examination zone 13, the X-ray beam 4 is incident on a two-dimensional detector unit 16 which is connected to the gantry 1. The detector unit comprises a number of detector rows which are arranged adjacent one another in the z direction and each of which comprises a plurality of detector elements. The detector rows are situated in planes perpendicular to the axis of rotation and on an arc of a circle about the radiation source S; however, they may alternatively describe an arc of a circle about the axis of rotation 14 or be arranged along a straight line. Each detector element provides a measuring value for a ray of the radiation beam 4 in each position of the radiation source.

The angle of aperture of the radiation beam, denoted by the reference $\alpha_{max}$ (the angle of aperture is defined as the angle enclosed by a ray, situated at the edge of the radiation beam 4 in a plane perpendicular to the axis of rotation, relative to the plane of the central ray defined by the radiation source S and the axis of rotation 14), determines the diameter of the cylinder within which the object to be examined is situated during the acquisition of the measuring values. The examination zone 13, or the object to be examined or the patient table, can be displaced parallel to the axis of rotation 14 by means of a motor 5. When the motors 2 and 5 are simultaneously activated, the radiation source S and the detector unit 16 perform a helical scanning motion about the examination zone 13. However, when the motor 5 for the transport in the z direction is stationary and the motor 2 rotates the gantry separately, the radiation source S and the detector unit 16 perform a circular scanning motion relative to the examination zone 13.

The measuring data acquired by the detector unit 16 is applied to an image processing computer 10 which reconstructs therefrom the absorption distribution in a part of the examination zone 13 and, for example, displays it on a monitor. The two motors 2 and 5, the image processing computer 10, the radiation source S and the transfer of the measuring values from the detector unit 16 to the image processing computer 10 are controlled by a suitable control unit 7.

Figure 2:
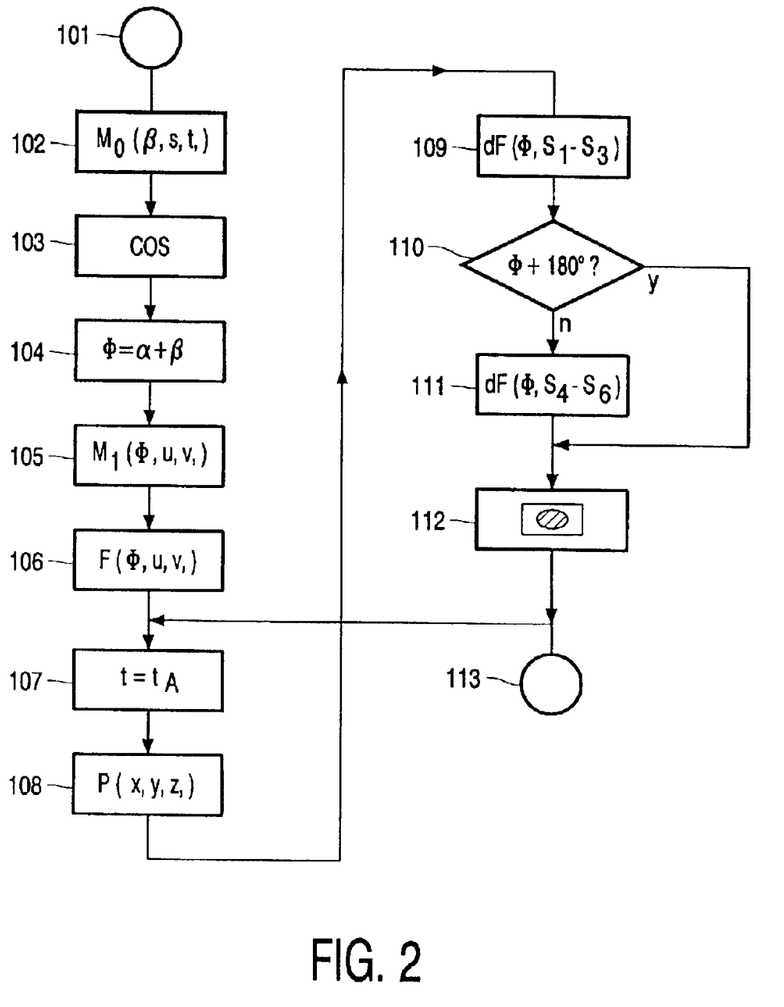
FIG. 2 shows a flow chart illustrating this method.

FIG. 2 illustrates the execution of a measuring and reconstruction method which can be carried out by means of the computed tomography apparatus shown in FIG. 1.

After the initialization in the block 101, the gantry rotates at a constant speed, resulting in a rotation period of, for example, 1 second or less. The radiation source S emits radiation, for example, a conical radiation beam, which traverses the examination zone and the measuring values acquired by the detector elements of the detector unit 16 are buffered and further processed in the image processing computer 10.

Figure 3:
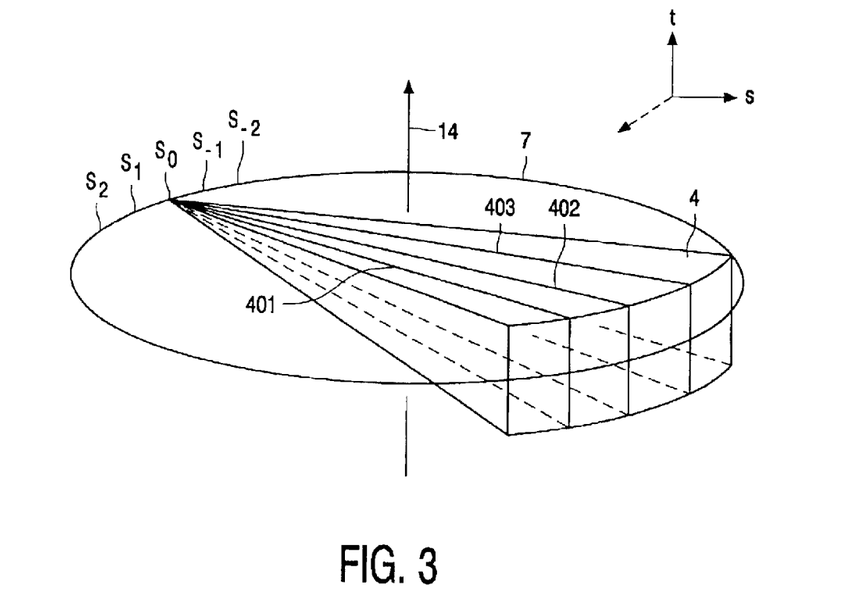
FIG. 3 shows a conical radiation beam produced in a radiation source position.

FIG. 3 shows the circular path 17 along which the radiation source S and the detector unit 16 move around the axis of rotation 14. The radiation beam 4 is shown for a given radiation source position $S_0$. This conical radiation beam can be decomposed into a plurality of flat fan beams which are situated in planes parallel to the axis of rotation, like the fan beams 401, 402, 403 in FIG. 3. The fan beams emanate from the same radiation source position and are detected by a respective column of detector elements of the detector unit 16, which column is directed parallel to the direction of rotation.

FIG. 3 indicates that the emitted conical radiation beam is also measured in other positions of the radiation source, for example, $S_{-2}$, $S_{-1}$, $S_1$ or $S_2$. These radiation source positions, or the radiation beams (4) emitted therein, may be characterized by a parameter $\beta$ which corresponds to the angle enclosed by the perpendicular from the radiation source position to the axis of rotation 14 relative to a reference plane which contains the axis of rotation (in conformity with the number of revolutions of the radiation source about the axis of rotation, $\beta$ may be larger than $2\pi$). The position of each fan beam in a radiation beam may be characterized by a parameter s which describes the position of the column of detector elements within the detector unit 16 which are exposed to the fan beam. Each ray within such a fan beam itself can be characterized by the parameter t which describes the position of the detector element within the column of detector elements which is exposed to the relevant ray or describes the distance between this detector element and a central plane which contains the circular path 17.

The acquired measuring values thus constitute a three-dimensional data set $M_0(\beta, s, t)$, each measuring value corresponding to a grid point of a regular cartesian grid in a three-dimensional ($\beta$, s, t) parameter space. The acquisition of the measuring values thus constitutes a scanning of the so-called object function (in this case of the line integral of the attenuation of the radiation) in a number of points which are regularly distributed in the ($\beta$, s, t) parameter space.

The acquisition of the measuring values in the step 102 and the processing of these measuring values in the subsequent steps 103 and further are carried out in parallel in time, so that the measuring values present are already processed while further measuring values are still being acquired.

In the step 103 the measuring values are multiplied by the cosine of the angle enclosed by the ray along which the measuring value has been acquired and a plane which is perpendicular to the axis of rotation. When the dimensions of the detector unit are small in the z direction, however, this step can be dispensed with, because in that case the angle is so small that the cosine of the angle is always approximately 1.

The data set $M_0(\beta, s, t)$ acquired in the step 102 and possibly modified in the step 103 is not yet optimum for further processing. Therefore, a so-called rebinning of the measuring values is performed in the steps 104 and 105. The data is then resorted and re-interpolated as if it had been measured with a different radiation source (a circular radiation source emitting parallel fan beams) and with a different detector (a flat, rectangular detector containing the axis of rotation). To this end, in the step 104 first the fan beams from different radiation source positions and being situated in mutually parallel planes are combined so as to form a respective group.

Figure 4:
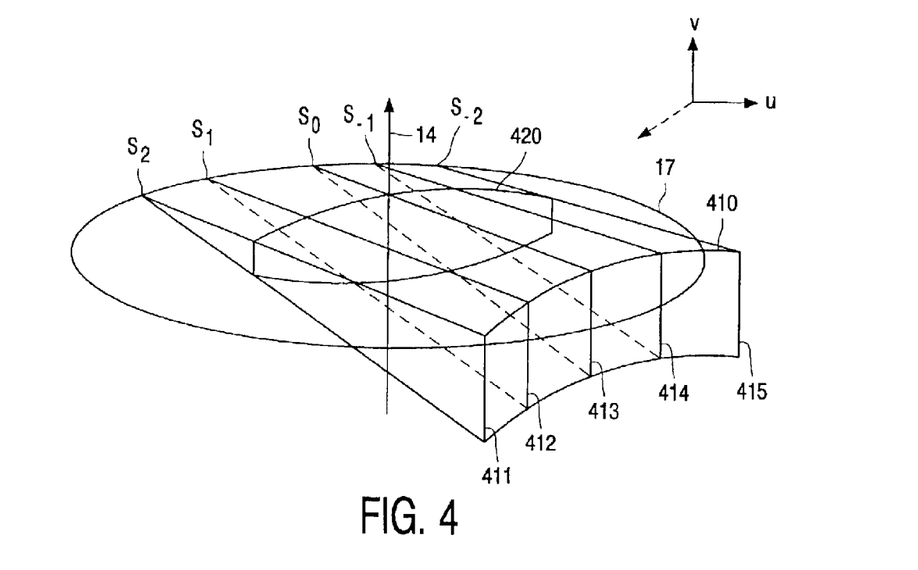
FIG. 4 shows a group of fan beams, formed by rebinning, in parallel planes.

FIG. 4 shows a group of fan beams thus formed. Each time one fan beam of each radiation source position $S_{-2}$ . . . $S_0$ . . . $S_2$ belongs to this group.

The fan beams associated with a group satisfy the condition:

$$\phi = \alpha + \beta \qquad (1)$$

Therein, $\phi$ is the projection angle at which a group of fan beams traverses the examination zone and which is enclosed relative to the other reference plane, containing the axis of rotation, by each fan beam of this group, $\alpha$ denotes the angle enclosed by the relevant fan beam in the original radiation beam (see FIG. 3) and a central plane determined by the axis of rotation 14 and the radiation source position (for example, $S_2$ which itself is defined by the angle $\beta$). Groups of fan beams of this kind are formed for different projection angles $\phi$ which deviate from one another by each time a given projection angle increment $d\phi$. When the fan beams of a radiation beam do not satisfy the equation 1, a corresponding fan beam must be determined by interpolation from the rays of neighboring fan beams of the radiation beam (FIG. 3).

The fan beams of a group, including the fan beams 411 . . . 415 shown in FIG. 4, define a radiation beam 410 which has a tent-like shape and is composed of fan beams which are situated in planes extending parallel to one another and parallel to the axis of rotation. FIG. 4 also shows the area of intersection 420 which is obtained when the radiation beam 410 is intersected by a plane which contains the axis of rotation 14 and extends perpendicularly to the planes of the fan beams 411 . . . 415. The upper and lower edges are curved outwards like a cushion, because the radiation source positions at the center are situated further from the plane of intersection than the radiation source positions at the edge.

In the step 105 a rectangular zone is defined while omitting the curved upper and lower edges of the area of intersection 420, and the rays of the fan beams of a group are calculated again by interpolation, that is, in such a manner that they puncture said rectangle in the area of intersection 420 at the grid points of a regular cartesian grid which are characterized by the co-ordinates u (perpendicular to the axis of rotation) and v (parallel to the axis of rotation). The rebinning thus transforms the measuring values $M_0(\beta, s, t)$ which are defined by a regular grid in the $(\beta, s, t)$ parameter space into measuring values $M_1(\phi, u, v)$ which are defined by a regular grid in the three-dimensional $(\phi, u, v)$ parameter space.

Because the part of the rays of the original radiation beam which are situated in the curved upper or lower region of the area of intersection 420 (that is, outside the rectangle for which the measuring values $M_1(\phi, u, v)$ are defined) is no longer used for the execution of the method, it is advantageous to design the collimator device 3 in such a manner that the conical radiation beam does not contain these rays. Instead of having straight edges extending perpendicularly to the axis of rotation, to this end the collimator device 3 should have edges which are curved inwards. The radiation dose whereto the patient is exposed would thus be reduced.

In the step 106 one-dimensional, ramp-like filtering of the measuring values $M_1(\phi, u, v)$ is performed. All measuring values having the same projection angle $\phi$ and the same parameter v are then subjected to filtering in which the transmission factor increases in a ramp-like fashion as a function of the frequency.

The data $F(\phi, u, v)$ thus filtered is subsequently used for the reconstruction of the absorption distribution in the examination zone by way of backprojection, be it that it is first stored in a buffer memory. During the subsequent reconstruction steps 107 and further, the steps 103 to 106 are continuously carried out on the measuring values still being acquired (in the step 102), resulting in a steady stream of data $F(\phi, u, v)$ thus filtered. From this stream of filtered data CT images which represent the object at different scanning instants are formed by a respective backprojection. In order to avoid the patient from being exposed to a radiation load without the measuring values thus formed being required for the reconstruction, the distance in time between successive imaging instants is shorter than the period of time required by the radiation source for a complete rotation around the axis of rotation 14.

Thus, a corresponding instant $t_A$ is selected in the step 107. This imaging instant is associated with a given radiation source position ($\beta$). However, because a given delay occurs between the acquisition of the measuring values and the formation of the filtered data from these measuring values in the step 106, the radiation source has meanwhile already passed this position. The backprojection comprises the selection of a voxel P(x, y, z) in the step 108 and the summing in the steps 109 to 111 of the contributions of the filtered data from rays which have previously struck the relevant voxel.

Figure 7:
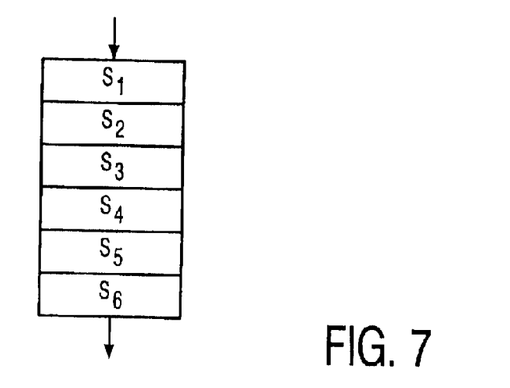
FIG. 7 shows a memory used for the backprojection.

For the explanation of the backprojection it is assumed that six CT images are to be reconstructed during each rotation of the radiation source, which CT images represent the object at each time six imaging instants associated with six radiation source positions which are regularly distributed along the circle 17. It is also assumed that prior to the imaging instant the filtered data is present for a projection angle range of 360° and that this data is stored in a memory. This memory is shown in FIG. 7 and has a number of segments $S_1$ to $S_6$ which corresponds to the number of imaging instants (six in the present example); these segments are capable of storing the data for a projection angle range of each time 60° and are organized in the form of a shift register in which the newly arriving data $F(\phi, u, v)$ replace the previous data. Consequently, after the step 107 the newest data $F(\phi, u, v)$ for a projection angle range of from $\phi_A-60°$ to $\phi_A$ is present in the first section $S_1$ for the imaging instant $t_A$, where $\phi_A$ is the projection angle of the last filtered data $F(\phi_A, u, v)$ entered. The second segment $S_2$ then contains the data for a projection angle range of from $\phi_A-120°$ to $\phi-60°$, whereas the third segment $S_3$ contains the data for a projection angle range of from $\phi_A-180°$ to $\phi-120°$, etc.

In the step 109 summing takes place of the contributions $dF(\phi, S_1-S_3)$ by filtered data which is stored in the segments $S_1$ to $S_3$ and associated with the rays which have irradiated the voxel from the projection angle range from $\phi_A$ to $\phi_A-180°$. Subsequently, in the step 110 it is checked for each projection angle $\phi(\phi<\phi_A-180°)$ whether the voxel has been irradiated from the projection direction $\phi+180°$ (and hence a contribution for the voxel was accumulated in the step 109). If this was the case, the next step 111 is skipped. In the step 111 the contributions $dF(\phi, S_4-S_6)$ by filtered data stored in the segments $S_4$ to $S_6$ and associated with rays which have irradiated the voxel from the projection angle range of from $\phi_A-180°$ to $\phi_A-360°$ are summed for the other projection directions.

The summing result is dependent on the position of the voxel P(x,y,z) in the examination zone. In this respect reference is made to the FIGS. 5 and 6.

Figure 5:
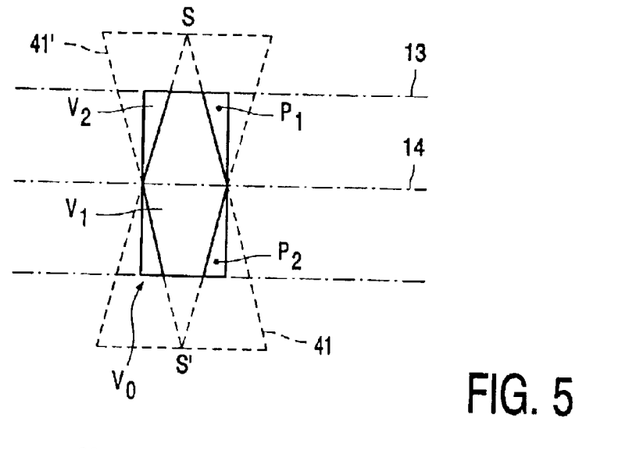
FIG. 5 shows the geometrical conditions in the examination zone in a representation containing the axis of rotation.

FIG. 5 shows, by way of dashed lines, one of the fan beams 41 which has been formed by rebinning and passes through the axis of rotation 14. The radiation source S is then situated vertically above the axis of rotation. Also shown is a fan beam 41' which is emitted from a radiation source position S' vertically below the axis of rotation 14. The edge rays of the two fan beams intersect at the axis of rotation 14 because of the symmetry of the arrangement and it can be demonstrated that these points of intersection define the width of the cylindrical volume $V_0$ in which the absorption distribution can be completely reconstructed. The absorption distribution in the object 13 to be examined cannot be reconstructed outside said volume $V_0$.

The volume $V_0$ can be subdivided into a first sub-volume $V_1$ and a second sub-volume $V_2$ which are separated from one another by the edge rays of the fan beams 41, 41'. The first sub-volume $V_1$ at the center is a rotationally symmetrical and discus-shaped zone, whereas the second sub-volume $V_2$ comprises all remaining zones to both sides of the first sub-volume $V_1$ within the volume $V_0$. All voxels within the first sub-volume $V_1$ are continuously exposed to radiation. However, the voxels in the second sub-volume $V_2$ are not continuously exposed to radiation. For example, the voxel $P_1$ which is situated above the axis of rotation 14 is not struck by the fan beam 41 (but is struck by the fan beam 41'), whereas the voxel $P_2$ which is situated therebelow and symmetrically relative to the axis of rotation 14 is struck by the fan beam 41 but not by the fan beam 41'.

Thus, the position of a voxel in the volume $V_0$ determines at which projection angles $\phi$ a contribution $dF(\phi, S_1-S_3)$ is obtained for the relevant voxel in the step 109.

Figure 6:
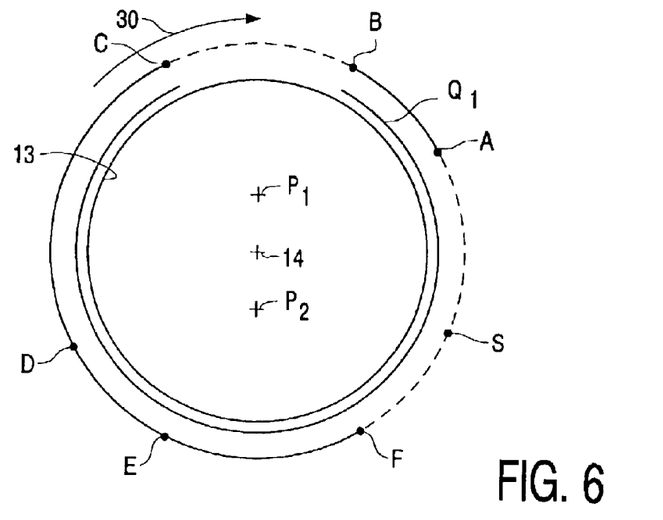
FIG. 6 shows the geometrical conditions in the examination zone in a representation oriented in a direction perpendicular thereto.

Reference is made to FIG. 6 for a further elucidation. FIG. 6 shows the examination zone 13 in a sectional view perpendicular to the axis of rotation 14. The arc of circle $\phi_1$ symbolizes the projection angle range wherefrom the voxel $P_1$ can be struck by radiation (this representation simplifies the conditions in a sense that the radiation source is situated at a distance from the axis of rotation which is significantly larger than the distance resulting from this arc). All voxels in the second sub-volume have such a projection angle range which amounts to at least 180° and less than 360° and may be situated in a different position relative to the axis of rotation.

FIG. 6 also shows a further circle which is partly denoted by a dashed line. The position of the radiation source at the imaging instant $t_A$ is denoted by the letter S. The position A is shown so as to be shifted through the angle $2\alpha_{max}$ relative to the position S, that is, against the direction of rotation in conformity with the arrow 30. This position defines the projection angle $\phi_A$ for which the measuring values derived from the rebinning up to the imaging instant $t_A$ are still suitable to form a complete group of fan beams (that is, a group which has traversed the entire cross-section of the examination zone). The positions B, C, D, E and F denote projection angles $\phi_B$, $\phi_C$, $\phi_D$, $\phi_E$ and $\phi_F$ which result from the rebinning of previously acquired measuring values.

The reconstruction of a voxel in the first sub-volume requires the filtered data of rays which are situated in the projection angle range of from $\phi_A$ to $\phi_D$, that is, in a projection angle range of 180°. The same holds for a part of the voxels in the second sub-volume $V_2$ when they have been acquired in all angular positions $\phi_A \ldots \phi_D$ by a fan beam at a corresponding projection angle such as, for example, the voxel $P_2$. In the steps 110 and 111 these voxels no longer receive a contribution from previously acquired data from the segments $S_4$ to $S_6$ of the memory.

However, this projection angle range does not suffice for the voxel $P_1$, because this voxel is not struck by any fan beam in the range from $\phi_B$ to $\phi_C$. For this voxel the filtered data of even earlier acquired measuring values (from the segments $S_4$ to $S_6$ of the memory) must be used. Because measurements from 180° shifted directions are equivalent in computed tomography, the missing data of fan beams from the range $\phi_B$ to $\phi_C$ can be replaced by filtered data of the fan beams from the projection angle range $\phi_E$ to $\phi_F$ which is situated diametrically opposite the projection angle range $\phi_B$ to $\phi_C$. This example demonstrates that so many previously acquired measuring data must be used until filtered data from a coherent range (in this case $\phi_C$ to $\phi_F$) of projection angles amounting to 180° is available for the relevant voxel ($P_1$). Only in that case will it be possible to assign contributions of fan beams from an overall projection angle range of 180° to this voxel in that case.

In this case there are two diametrically oppositely situated projection angle ranges for the voxel $P_1$, that is, the ranges $\phi_A-\phi_B$ and $\phi_D-\phi_E$. This fact is recognized in the step 110 and, therefore, this voxel does not receive a contribution for the projection angle range $\phi_D-\phi_E$ from the segments $S_4$ to $S_6$ of the memory. However, there is a contribution from the segments $S_4$ to $S_6$ for the range $\phi_E-\phi_F$, because the voxel has not received a contribution from the range $\phi_B$ to $\phi_C$.

However, there are also other possibilities for the processing of the filtered data from these ranges. This is because contributions from the projection angle range $\phi_A-\phi_B$ as well as from the range $\phi_D-\phi_E$ can be summed with two weighting factors (for example, 0.5) for the pixel $P_1$, the sum of said factors being equal to the weight with which the filtered data of fan beams from the range $\phi_C-\phi_D$ or $\phi_E-\phi_F$ are taken into account during the backprojection.

The CT image thus reconstructed for the absorption of the radiation in the volume $V_0$ is suitably displayed on the monitor 11 (step 112). In the mean time the steps 103 to 106 are continuously applied to the measuring values still being acquired (in the step 102). For a later imaging instant a further CT image is reconstructed from the resultant stream of filtered data, said CT image being associated, for example, with a radiation source position which has been shifted forwards through, for example, 60° in the direction of rotation.

For the last data formed filtered data $F(\phi, u, v)$ is stored for a projection angle range of 60° in the first segment $S_1$ of the memory, the previously stored data then being moved to the next segment. The oldest data, previously stored in the last segment $S_6$, is erased. The execution of the loop comprising the steps 107 to 112 is then repeated until CT fluoroscopy is terminated by the user in the step 113.

It has been assumed in the foregoing that the radiation source and the detector unit rotate about the axis of rotation 14 whereas the examination zone or the object to be examined which is present therein is stationary. This is necessary in the case of medical examinations. In the case of industrial examinations of, for example, workpieces, the object to be examined may rotate and the radiation source and the detector unit may remain stationary. The invention can also be carried out in such a case. The projection angle $\phi$ and the radiation source $\beta$, however, are then defined by the angular position of the object to be examined.

The invention has been described with reference to the preferred embodiment. Obviously, modifications and alterations will occur to others upon reading and understanding the preceding description. It is intended that the invention be construed as including all such modifications and alterations insofar as they come within the scope of the appended claims or the equivalents thereof.

What is claimed is:

1. A fluoroscopic computed tomography method which includes the steps of:

irradiating an object to be examined by means of a conical radiation beam which is emitted by a radiation source while the object to be examined or the radiation source rotates about an axis of rotation;

acquiring, using a detector unit, measuring values which are dependent on the intensity in the radiation beam beyond the object to be examined;

generating CT images which represent the object to be examined at imaging instants which are situated at a distance in time from one another which is shorter than the period of time required for a rotation of the object to be examined or the radiation source about the axis of rotation, the generation of CT images including the following steps:

rebinning the measuring values so as to form a number of groups, each group containing the measuring values of fan beams which are formed during the irradiation and are situated in planes extending parallel to one another and to the axis of rotation;

one-dimensional filtering of the data of each group as produced by the rebinning in order to produce filtered data;

backprojecting the filtered data of a plurality of groups, for each voxel to be reconstructed there being used filtered data from the last fan beams formed prior to the relevant imaging instant, said fan beams having irradiated the relevant voxel from an overall projection angle range of 180°.

2. A fluoroscopic computed tomography method as claimed in claim 1, in which the filtered data of fan beams which have irradiated the relevant voxel from projection angle ranges ($\phi_A$–$\phi_B$ and $\phi_D$–$\phi_E$) which have been shifted 180° relative to one another and are situated within the overall projection angle range of 180° are summed in a weighted fashion in order to reconstruct the absorption of voxels which are only temporarily present in the fan beam.

3. A fluoroscopic computed tomography method as claimed in claim 1, in which the reconstruction of the absorption in voxels which are only temporarily present in the fan beam utilizes, from among the filtered data of the fan beams which have irradiated the voxel from directions which are shifted 180° relative to one another and are situated within the overall projection angle range of 180°, only the data ($\phi_A$–$\phi_B$) of the last fan beam formed.

* * * * *